United States Patent [19]
Hiot et al.

[11] Patent Number: 5,330,476
[45] Date of Patent: Jul. 19, 1994

[54] PROTECTIVE CAP FOR AN OSTEOSYNTHESIS PIN AND ASSEMBLY INCLUDING THIS CAP AS WELL AS AN INSTRUMENT FOR FIXING IT ON THE PIN

[75] Inventors: Jean-Claude Hiot, 80300 Bouzincourt; Christophe Obry, Clinique Pauchet de Butler, rue Albérie de Coloue, 80000 Amiens; Patrick Letot, Domaine "Les Gouttes", 03160 Saint Aubin le Monial; Patrick Sueur, 15, rue des Majots, 80000 Amiens, all of France

[73] Assignees: Christophe Obry, St. Fucien; Jean-Claude Hiot, Bouzincourt; Patrick Sueur, Amiens; Patrick Letot, Dieppe, all of France

[21] Appl. No.: 976,921

[22] Filed: Nov. 18, 1992

[30] Foreign Application Priority Data

Nov. 18, 1991 [FR] France .................. 91 14184

[51] Int. Cl.⁵ .................................. A61F 5/00
[52] U.S. Cl. ................................. 606/60; 606/59; 606/72; 606/74
[58] Field of Search ............ 606/1, 53, 54, 56, 57, 606/59, 60–62, 64–67, 72–74, 86, 87, 103–105

[56] References Cited

U.S. PATENT DOCUMENTS

| | | | |
|---|---|---|---|
| 2,081,293 | 5/1937 | Davis . | |
| 4,135,505 | 1/1979 | Day | 606/73 |
| 4,360,012 | 11/1982 | McHarrie et al. | 606/54 |
| 4,763,644 | 8/1988 | Webb | 606/61 |
| 4,823,781 | 4/1989 | Buchanan | 606/54 |
| 4,887,596 | 12/1989 | Sherman | 606/73 |
| 4,976,712 | 12/1990 | VanderSlik . | |
| 5,087,258 | 2/1992 | Schewior | 606/56 |
| 5,108,399 | 4/1992 | Eitenmuller | 606/76 |
| 5,129,900 | 7/1992 | Asher et al. | 606/73 |
| 5,133,717 | 7/1992 | Chopin | 606/73 |

FOREIGN PATENT DOCUMENTS

| | | | |
|---|---|---|---|
| 2633822 | 1/1990 | France . | |
| WO9116860 | 11/1991 | PCT Int'l Appl. . | |
| 1146017 | 3/1985 | U.S.S.R. | 606/57 |

Primary Examiner—Stephen C. Pellegrino
Assistant Examiner—Jeffrey A. Schmidt
Attorney, Agent, or Firm—Sughrue, Mion, Zinn, Macpeak & Seas

[57] ABSTRACT

A cap (1) has a housing (9) adapted in order to receive one end of the pin (2), and a tapped hole (11) opening out transversely in this housing, adapted in order to receive a fixing screw (12) allowing the pin (2) and the cap (1) to be solidly attached together; the screw (12) is initially made in a single piece with the terminal part (4) of a handle (7) of the fixing instrument (3), an embrittled zone (13) being made at the transition between the screw and the terminal part (4). The surgeon first covers the pin (2) with the cap (1), then screws the screw (12) until it locks the pin (2), and the end of screwing causes the embrittled zone (13) to rupture, so that only the screw (12) remains locked in place in the cap (1) fixed to the pin (2). This cap prevents any migration of the pin and protects the neighbouring tissues.

7 Claims, 4 Drawing Sheets

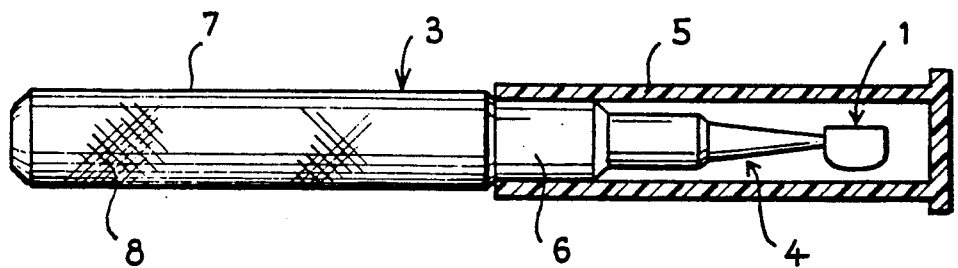
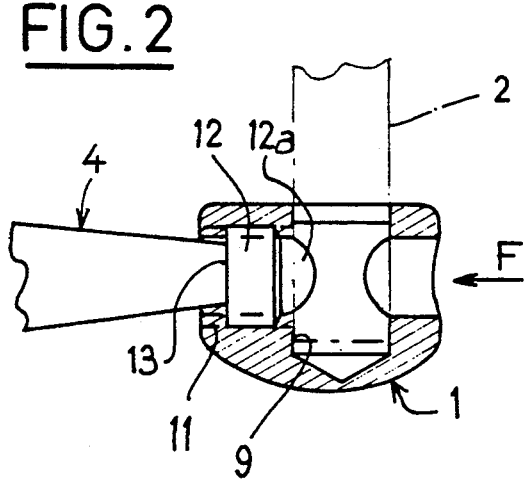
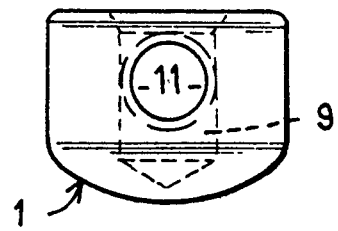
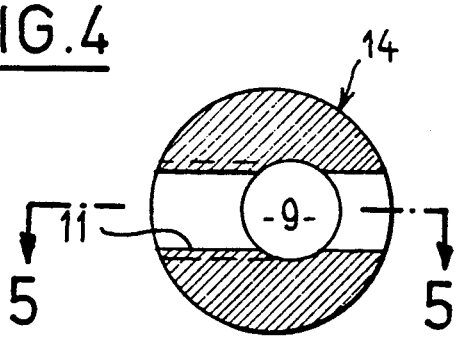
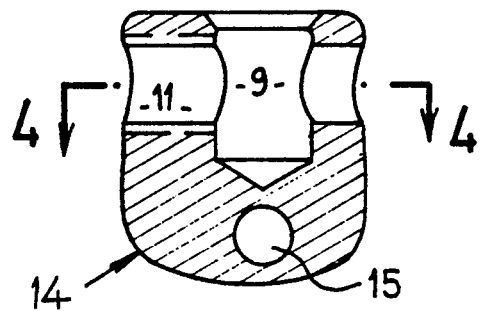

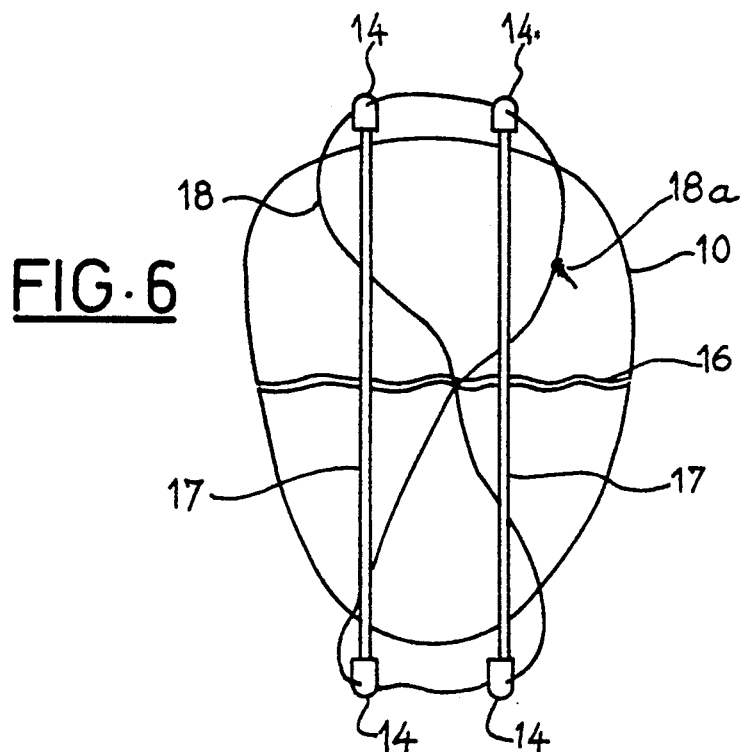
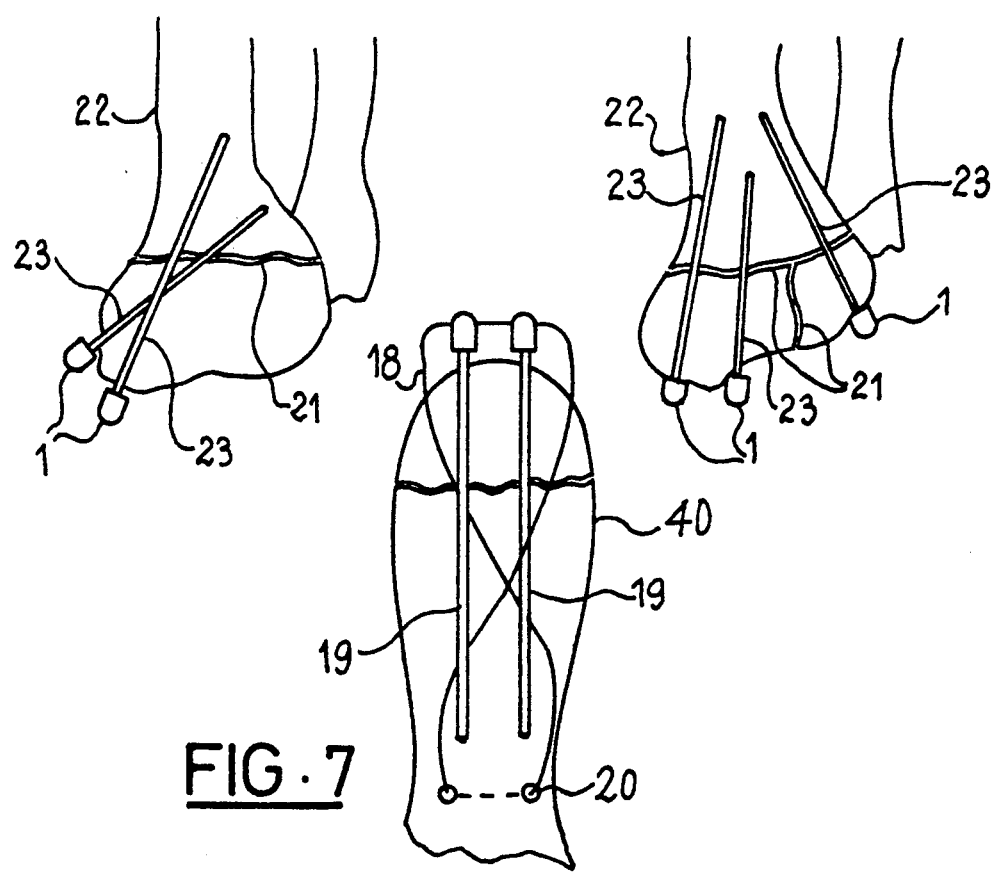

PROTECTIVE CAP FOR AN OSTEOSYNTHESIS PIN AND ASSEMBLY INCLUDING THIS CAP AS WELL AS AN INSTRUMENT FOR FIXING IT ON THE PIN

BACKGROUND OF THE INVENTION

The subject of the present invention is a protective cap for an osteosynthesis pin as well as an assembly including this cap and an instrument for fixing the cap on the pin.

It is known that pins used in osteoarticular pathology, in particular to hold two parts of a fractured bone aligned, are introduced for this purpose into the osseous tissue on either side of the fracture. They must not migrate during the reduction of the fracture. In fact, if the unprotected pin projects out of the osseous tissue, this may cause tendinous ruptures, lesions of neurovascular elements, lesions of the cutaneous layer, secondary infection vectors, and may furthermore make subsequent extraction of this pin difficult.

Hitherto, either the pin has been left in place as it is, with the risks of subsequent complications or of migration, or its end has been covered with a crimped knob, or this end is bent; however this last solution does not in fact give complete satisfaction, because the osteosynthesis may be endangered by pulling apart the reduction of the fracture.

SUMMARY OF THE INVENTION

The object of the invention is to provide a satisfactory solution to the problem explained hereinabove.

According to the invention, the protective cap for the pin includes a housing adapted in order to receive one end of the pin, and a tapped hole opening out transversely in this housing, adapted in order to receive a fixing screw allowing the pin and the cap to be solidly attached together.

According to one characteristic of the invention, the screw has a brittle zone allowing it to rupture at the end of screwing and allowing the screw to be locked in the transverse hole.

Such a cap forms at the end of the pin a prominence which effectively opposes any undesired displacement of this pin.

The subject of the invention is also an assembly allowing fitting of the cap and locking of its screw on the pin in order to fix the cap to the latter.

According to the invention, this assembly includes a cap and an instrument for fixing of the cap on the pin, provided with a terminal part made in a single piece with the screw, a brittle zone for rupture at the end of screwing being made between the screw and the said terminal part.

Thus the screw for locking the cap on the pin initially forms an integral part of its positioning tool, from which it is detached only at the end of screwing, by rupture of the brittle zone. This arrangement avoids the use of a screwdriver, which would be particularly difficult under the conditions of a surgical operation and taking into account the small dimensions of the screw and of the cap.

Other characteristics and advantages of the invention will emerge during the description which is to follow and which is made with reference to the attached drawings which illustrate several embodiments thereof by way of non-limiting examples.

BRIEF DESCRIPTION F THE DRAWINGS

FIG. 1 is a partial elevation and partial longitudinal section on an enlarged scale of a first embodiment of the assembly which is the aim of the invention, including a cap and an instrument for fixing the cap on the pin, FIG. 2 is a partial cross-section and partial elevation of one embodiment of the cap on an enlarged scale, as well as of the screw for fixing it on the pin and of the terminal part of the support instrument for the screw.

FIG. 3 is an elevation of the cap along the direction of the arrow F in FIG. 2.

FIG. 4 is a cross-section along 4/4 in FIG. 5 of a second embodiment of the cap implant according to the invention.

FIG. 5 is a cross-section along 5/5 in FIG. 4.

FIG. 6 is an elevation of a first application of the protective cap according to the invention for the reduction of a patellar fracture.

FIG. 7 is a rear view of the upper end of a fractured cubitus (olecranon) fitted with a pin and cap implant system according to the invention.

FIG. 8 is a diagrammatic elevation of an application of the invention to the reduction of a fracture of the lower end of the radius.

FIG. 9 is a diagrammatic elevation of an application of the invention to a fracture of the lower end of the radius.

DESCRIPTION OF PREFERRED EMBODIMENTS

Figure 10:
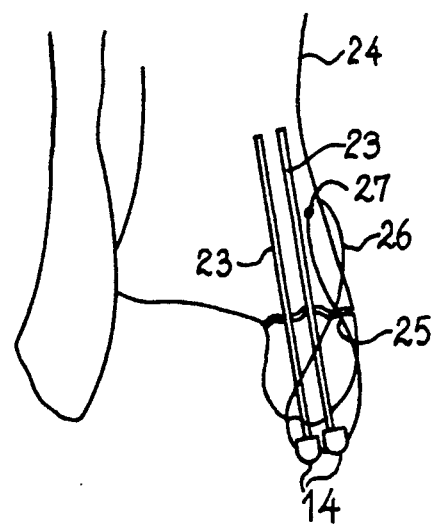
FIG. 10 is a diagrammatic elevation of an application of the invention to a malleolar ankle fracture.

The device represented in FIG. 1 includes a protective cap 1 for an osteosynthesis pin such as 2 (FIG. 2), an instrument 3 for fixing of the cap 1 on the pin, this instrument being provided with a terminal part 4 for supporting the cap 1, and finally a protective cover 5 covering the terminal part 4 and the cap 1. The cover 5, made for example from any appropriate plastic material, has a tubular shape and may be secured by friction on a cylindrical base 6 coaxial with the terminal part 4. This base 6 is extended by a handle 7 for manual gripping, whose surface is preferably covered with bumps, for example a knurling 8.

The cap 1, represented in detail in FIGS. 2 and 3, includes a housing 9 formed by a blind hole adapted in order to receive one end of the pin 2. In the cap implant 1, there is furthermore made a tapped hole 11 opening transversely in the housing 9, and adapted in order to receive a screw 12 allowing the pin 2 and the cap 1 to be solidly attached together. In the embodiment represented, the hole 11 passes right through the cap 1, perpendicularly to the axis of the cylindrical housing 9, only its part intended to receive the screw 12 being tapped.

The screw 12 has on one end thereof a head 12a adapted to match the cylindrical surface of the pin 2. The screw 12 is made in a single piece with the terminal part 4 of the handle/screw 3, and has, at the junction of its opposite end with this part 4, a brittle zone 13 allowing it to rupture at the end of screwing and thus allowing the screw 12 to be detached from the neck forming the terminal part 4.

The fitting of the cap 1 and its fixing to the pin 2 are performed very simply, in the following manner.

After having removed the cover 5, the surgeon, holding the handle 7 in his hand, brings the cap 1 up to the end of the pin 2 which he introduces into the housing 9, until its tip abuts upon the bottom of this housing. Then, the screw 12 being only partially driven into its hole 11, the surgeon starts to screw it by rotating the tool 3 like a screwdriver. At the end of screwing, the head 12a of the screw 12 comes to fit tightly against the pin 2 which it locks in translation and in rotation with respect to the cap 1. Then, by applying force to the handle 7, the surgeon causes the rupture of the brittle zone 13, then situated inside the tapped hole 11. The screw 12 is then in place and fixes the cap 1 to the pin 2.

The second embodiment of the cap 14, represented in FIGS. 4 and 5, differs from the previous one in that the body of the cap is larger and pierced by a bore 15, directed preferably perpendicular to the axis of the housing 9 and therefore to the pin 2. The bore 15 passes right through the cap 14, and allows the passage of a tying wire or an osseous brace, as will be described in more detail hereinbelow.

Of course, for a given size of the cap 1 or 14, the cavity 9 receiving the pin 2 may have a variable diameter, adapted to that of the pin, which may be unthreaded, or alternatively partially or completely threaded.

A number of examples of implementation of the invention will now be described with reference to FIGS. 6 to 17.

FIG. 6 illustrates the application of the invention to the fracture 16 of a patella 10: the device comprises two pins 17, both of whose ends are covered with a cap implant 14 through the holes 15 in which a wire 18, for example made of steel, passes. This wire, both of whose extremities are knotted at 18a, forms a tie or brace for holding the two parts of the fractured patella in compression.

FIG. 7 is a rear view of the upper end of a fractured cubitus 40 ( olecranon ), fitted with two pins 19 each provided with a cap 14, through which passes a steel wire 18 whose ends have been knotted so as to form a closed loop which passes through an osseous canal 20.

FIG. 8 shows the lower end of a radius 22, with two fracture lines 21, fitted with a device according to the invention with three pins 23, whose ends projecting from the radius 22 are each covered with a cap 1. The arrangement represented in FIG. 8 constitutes an intrafocal pinning after Kapandji.

FIG. 9 shows a radius 22 whose lower end has single fracture line 21 and which is provided with two crossed pins 23, whose ends projecting out of the radius are each covered with a cap 1. This is a styloid pinning.

FIG. 10 illustrates a mounting according to the invention of two pins 23 on an ankle 24 which has suffered an internal malleolar fracture 25. Each pin 23 has its end projecting externally to the ankle 24 covered by a cap 14 through which passes a wire 26, for example made of steel, forming a closed loop which passes through a tibial transosseous canal 27. Such a device can be applied to the internal or external malleolus.

Figure 11:
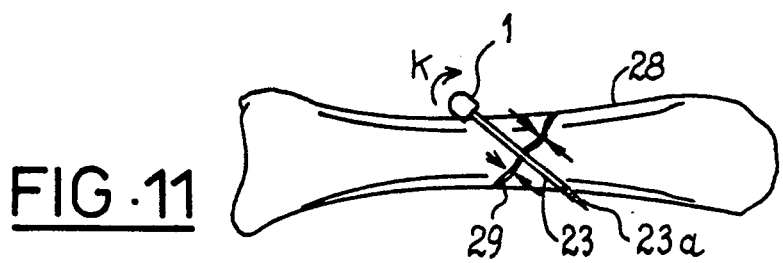
FIG. 11 is an elevation of an application of the invention to the fracture of a metacarpal, or of a phalanx with compression screwing.

FIG. 11 shows a metacarpal 28 whose fracture 29 is passed through by a pin 23. The distal end 23a of the pin 23 is threaded and passes through the cortical, while the proximal end is covered with a protective cap 1. The assembly of the pin 23 and the cap 1 is screwed, by means of pincers as indicated by the arrow K, in order to develop a compression at the fracture focus. This compression is induced by the slight displacement in translation of the pin caused by its rotation. This is applicable to the other bones of the locomotor apparatus.

Figure 12:
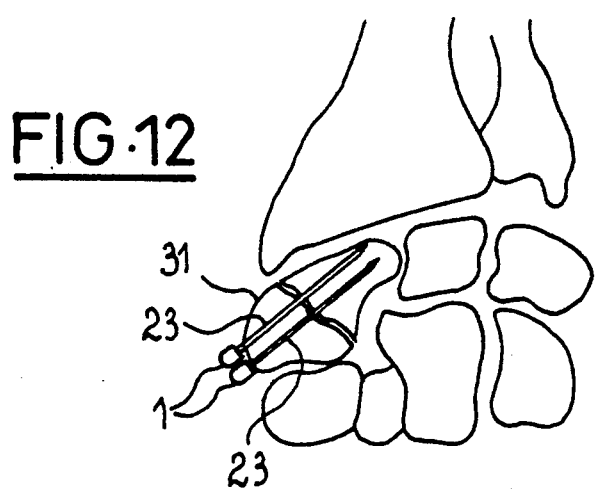
FIG. 12 is a diagrammatic elevation of an application of the invention to the surgical treatment of a scaphoid fracture or of a pseudoarthrosis of the scaphoid.

FIG. 12 shows a fractured carpal scaphoid 31, provided with two pins 23 whose ends outside the scaphoid are covered with a cap 1. Such a device can be applied to the surgical treatment of pseudoarthoses of the carpal scaphoid, combined or uncombined with an osseous graft, to the other bonelets of the carpus or of the tarsus, to the tarsus in fractures/luxations concerning the tarsus and the metatarsus, or to any other fracture pathology of the tarsus and of the metatarsus.

Figure 13:
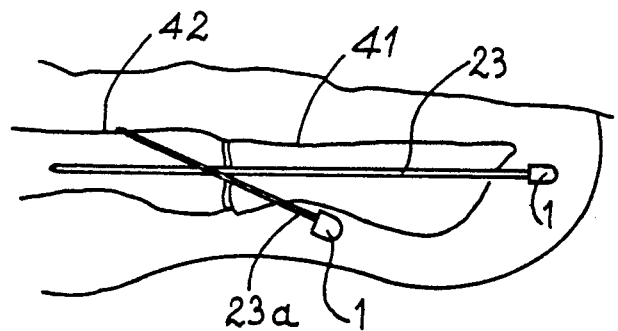
FIG. 13 is a diagrammatic elevation of an application of the invention to the arthrodesis of a digital joint.

FIG. 13 is an example of application of the invention to an arthrodesis (fusion of the two parts of the joint to each other) of a digital joint, such as the distal (or proximal) interphalangial. The two parts 41, 42 of the fractured bone are held in alignment by an axial pin 23 (smooth or threaded) supplemented by a small antirotation pin 23a, oblique with respect to the pin 23 so as to prevent either of the parts of the bone from rotating with respect to the other. Each of the two pins is covered with a cap 1.

Figure 14:
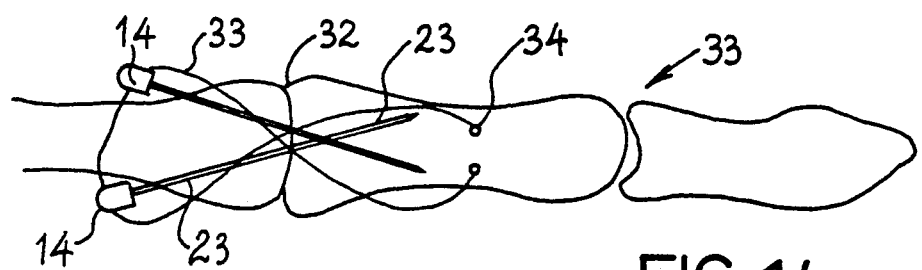
FIG. 14 is a diagrammatic elevation of an application of the invention to the arthrodesis of a metacarpophalangeal Joint of the thumb.

FIG. 14 illustrates an arthrodesis of the metacarpophalangial joint 32 of the thumb 33, or of the metatarsophalangial joint of the hallux. The device here comprises two pins 23 each provided with a cap 14 through which a wire 33 passes following a transosseous passage 34. Such a device is also applicable to the interphalangial joint of the thumb and of the hallux.

Figure 15:
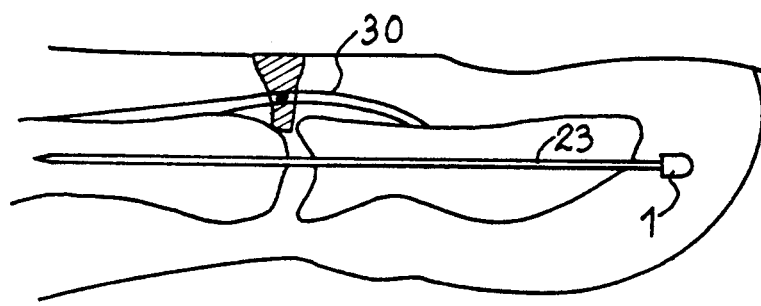
FIG. 15 is a diagrammatic elevation of an application of the invention to the temporary locking of a digital joint.

FIG. 15 shows a protection of a suture of the distal extensor apparatus (30) with interim locking of the distal interphalangial joint by a pin 23 provided with a cap 1 (this pin is to be held for 4 to 6 weeks).

Figure 16:
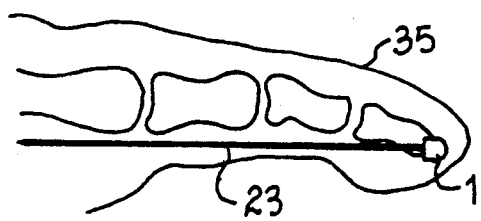
FIG. 16 is a diagrammatic elevation of an application of the invention in which a pin fitted with its protective cap is used as a guide for a claw toe after surgical correction of the deformation.

FIG. 16 shows a claw toe 35, in the digital canal of which there has been introduced, level with the bone, a guide pin 23 provided with a cap 1, after an arthroplastic moulding of the proximal interphalangial joint of the toe.

Figure 17:
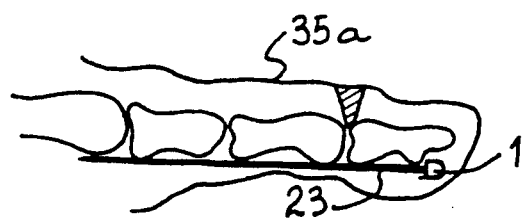
FIG. 17 is a similar view to FIG. 16 in which the pin is used as a guide for a hammer toe.

FIG. 17 shows a hammer toe 35a on which a distal interphalangial tenodermodesis has been performed, then into the digital canal of which a guide pin 23 has temporarily been fitted.

In addition to the advantages already mentioned, the protective cap and the assembly of which it forms a part have the following advantages.

1. The cap 1, 14 protects the neighbouring tissues, opposing any untimely displacement of the pin or migration.
2. The protective cap, fitted under the cutaneous layer, is easily locatable manually by feeling, which facilitates ablation of the pin by the surgeon. Thus for the latter the constraint of having to use a brightness amplifier is removed, which allows him a time saving and saves him from the radiations emitted by the brightness amplifier.

In corollary, the extraction of the pins after union of the fracture does not lead to any significant lesion by untimely searching for the pins, and therefore makes the surgical operation less "invasive" than has been the case hitherto. The ablation of the pins provided with a protective cap according to the invention is thus made relatively easy "remotely" from the fitting (that is to say after some time).

3. The implant constituted by the protective cap according to the invention allows the surgeon to choose a pin of the desired length. It is in fact sufficient to fit the pin, to cut it to the chosen length and to fix the protective cap thereto. This has a considerable advantage over the self-breaking pins with predetermined sizes of the prior art. These pins, protected by an endpiece, are most usually available in 0.5 cm intervals. They also have the drawback of rupture downstream of the protective knob, thus causing the loss of all the advantages of a protective endpiece for the pin. Furthermore, the predetermination of the lengths may require the pointed extremity of the pin to extend through the opposite cortical, which is a source of irritation for the neighbouring tissues.

4. The protective implant according to the invention may, within a fracture focus or arthrodesis, allow the creation of a certain degree of compression, by the use of pins threaded at their distal ends, the cap being placed in the proximal position (FIG. 11).

5. The protective cap 1, 14 according to the invention has great simplicity of use and may be fitted to pins which are completely or partially threaded or unthreaded.

The use of metal or textile wires constituting braces is of interest in a number of applications: patellar fracture (FIG. 6), fracture of the olecranon (FIG. 7), the proximal ends of the pins protected by the caps 14 allowing fitting of a bracing wire 18. These braces can also be used in other applications such as those already mentioned in a non-limiting manner (FIGS. 10 and 14).

What is claimed is:

1. A protective cap (1, 14) for an osteosynthesis pin (2), said cap comprising: a housing (9), for receiving one end of the pin in a longitudinal direction; and a tapped hole (11) which opens out transversely in said housing, and which receives a fixing screw (12) having on one end thereof a head for (12a) matching a cylindrical surface of the pin, and on an opposite end thereof an integral terminal part (4), said fixing screw allowing the pin and the cap to be solidly attached together; wherein said screw (12) has, at its junction with said terminal part, a brittle zone (13) allowing said screw and said terminal part to rupture at the brittle zone at the end of screwing and allowing said screw to be locked in the transverse hole (11).

2. Cap according to claim 1, characterised in that it is pierced by a bore (15) allowing the passage of a wire (18, 33 . . . ) for tying a bone (10, 40 . . . ) intended to receive the pin (2) fitted with this cap (1, 14).

3. The cap according to claim 1, wherein said terminal part (4) has an integral extension (6, 7) which forms an instrument handle (7) which is manually grippable for placing the cap on said one end of the pin (2).

4. An assembly, including a protective cap, for fixing the protective cap to an osteosynthesis pin (2), said assembly comprising: a fixing screw (12); a housing (9) for receiving one end of the pin in a longitudinal direction, and which has a tapped hole (11) which opens out transversely in said housing, and which receives said fixing screw (12), said fixing screw having on one end thereof a head for (12a) matching a cylindrical surface of the pin, and on an opposite end thereof an integral terminal part (4); a transversely extending instrument handle (7) integral with said terminal part (4), said fixing screw allowing the pin and the cap to be solidly attached together; wherein said screw (12) has, at its junction with said terminal part, a brittle zone (13) allowing said screw (12) and said terminal part (4) to rupture at the brittle zone at the end of screwing and allowing said screw to be locked in the transverse hole (11).

5. The assembly according to claim 4, characterised in that the brittle zone (13) is a narrowing of the terminal part (4), forming a neck at the junction with the screw (12).

6. The assembly according to claim 5, characterised in that the instrument handle (3) is covered with a knurling.

7. The assembly according to claim 6, characterised in that it comprises a protective cover (5) covering the terminal part (4) and the cap (1).

* * * * *